United States Patent [19]
Fung et al.

[11] Patent Number: 6,143,899
[45] Date of Patent: Nov. 7, 2000

[54] CHEMICAL PROCESS

[75] Inventors: Alexander Pai-Yung Fung, Martinez; David Dale Friese, Orinda; Erwin Michael Seidel, Clayton, all of Calif.; Alan John Whitton, Falkirk, United Kingdom; Alastair Iain Currie Stewart, Grangemouth, United Kingdom; Jennifer Ann White, Grangemouth, United Kingdom; Raymond Vincent Heavon Jones, Grangemouth, United Kingdom; John Desmond Hunt, Haslemere, United Kingdom

[73] Assignee: Zeneca Limited, United Kingdom

[21] Appl. No.: 09/390,049

[22] Filed: Sep. 3, 1999

[30] Foreign Application Priority Data

Sep. 3, 1998 [GB] United Kingdom .................. 9819235

[51] Int. Cl.[7] ................................................. C07D 211/72
[52] U.S. Cl. ............................................. 546/303
[58] Field of Search ................................. 546/303

[56] References Cited

U.S. PATENT DOCUMENTS

| 3,355,456 | 11/1967 | Sexton | 260/297 |
|---|---|---|---|
| 3,609,158 | 9/1971 | Torba | 260/295 |
| 3,711,486 | 1/1973 | Torba et al. | |
| 4,038,396 | 7/1977 | Shen et al. | 424/256 |
| 4,108,629 | 8/1978 | McKendry | 71/94 |
| 4,249,009 | 2/1981 | Bailey | 546/345 |
| 4,455,313 | 6/1984 | Ehr | 424/263 |
| 4,474,599 | 10/1984 | Rogers et al. | 71/92 |
| 4,942,239 | 7/1990 | Orth et al. | 546/290 |
| 4,976,946 | 12/1990 | King | 423/490 |
| 5,973,159 | 10/1999 | Lilley et al. | 546/303 |

FOREIGN PATENT DOCUMENTS

| 769015 | 12/1971 | Belgium . |
|---|---|---|
| 1075468 | 9/1987 | Japan . |
| 63-48268 | 2/1988 | Japan . |
| 288628 | 7/1929 | United Kingdom . |
| 98/40355 | 9/1998 | WIPO . |

OTHER PUBLICATIONS

Parker, Edwin D. and Shive, William; "Substituted 2–Picolines Derived from 6–Amino–2–picoline," *JACS*, 69, pp. 63–67 (1947).

Chemical Abstracts, 23, 607 (1929).

Klingsberg, Erwin, ed., *Pyridine and Its Derivatives*, Part Two, pp. 345–352, 408, 415 (1961).

Klingsberg, Erwin, ed., *Pyridine and Its Derivatives*, Part Three, pp. 571, 871 (1962).

*Primary Examiner*—John Kight
*Assistant Examiner*—Binta Robinson
*Attorney, Agent, or Firm*—Thomas R. Savitsky

[57] ABSTRACT

A process for the preparation of 2-hydroxy-6-trifluoromethylpyridine which comprises reacting 2-fluoro-6-trifluomethylpyridine or a mixture of 2-fluoro-6-trifluoromethylpyridine and 2-chloro-6-trifluoromethylpyridine with an alkali metal hydroxide at a temperature of from 50° C. to 160° C. and acidifying the product so formed.

9 Claims, No Drawings

CHEMICAL PROCESS

This invention relates to a chemical process and, more particularly, to a process for preparing 2-hydroxy-6-trifluoromethylpyridine which is useful in the manufacture of certain agricultural products.

Processes for preparing 2-hydroxypyridines by the hydrolysis of 2-chloropyridines are described in the chemical literature. Thus, UK Patent No. 288,628 describes the preparation of 2-hydroxypyridine by the hydrolysis of 2-chloropyridine with solid potassium hydroxide at 175° C. It also describes the preparation of 2-hydroxy-5-nitropyridine by the hydrolysis of the corresponding chloropyridine with (a) concentrated hydrochloric acid in a bomb tube at 150° C. and (b) with 2-normal caustic soda lye under reflux.

U.S. Pat. No. 4,942,239 describes the preparation of 2-hydroxypyridine by the hydrolysis of 2-chloropyridine with an aqueous concentrated potassium hydroxide solution in the presence of a tertiary alcohol, such as tert-butyl or tert-amyl alcohol, under reflux at atmospheric pressure. A solvent-based process has also been described for the preparation of 2-hydroxy-6-trifluoromethylpyridine in, for example, U.S. Pat. No. 3,609,158. In this patent 2-chloro-6-trifluoromethylpyridine in dimethylsulphoxide (DMSO) is hydrolysed by heating with aqueous sodium hydroxide under reflux.

2-Hydroxy-6-trifluoromethylpyridine can readily be prepared in good yield by the alkaline hydrolysis of 2-chloro-6-trifluoromethylpyridine in a solvent such as DMSO or tert-amyl alcohol. On a large scale, however, solvent-based processes are generally undesirable because of the environmental and safety implications and the need for solvent recovery systems.

The treatment of 2-chloro-6-trifluoromethylpyridine with 35% hydrochloric acid at 150° C. results in only a trace of hydrolysis and with aqueous sodium hydroxide under reflux may, result in no hydrolysis at all. Treatment with solid base leads to hydrolysis but causes processing difficulties.

The process of the present invention, which may be operated in the absence of an organic solvent, is high yielding and provides a more practical procedure.

Thus, according to the present invention, there is provided a process for the preparation of 2-hydroxy-6-trifluoromethylpyridine which comprises reacting 2-fluoro-6-trifluoromethylpyridine or a mixture of 2-fluoro-6-trifluoromethylpyridine and 2-chloro-6-trifluoromethylpyridine with an alkali metal hydroxide at a temperature of from 50° C. to 160 ° C. and acidifying the product so formed.

The alkali metal hydroxide is preferably sodium hydroxide or potassium hydroxide, the latter generally being the more effective. It may be used in aqueous form, in which case, the aqueous base solution strength should be at least 5% w/v and is suitably in the range of 9 to 85% w/v, for example, 9 to 60% w/v, typically up to about 50% w/v. Alternatively, if the starting material contains a high level of the chlorinated pyridine component, for example, 50 or more, it is advantageous to dissolve it in a suitable solvent such as a tertiary alcohol, for example tert-butyl or tert-amyl alcohol, an aromatic solvent such as xylene, an inert ketone, or a polar aprotic solvent such as dimethylsulphoxide, and to slurry the alkali metal hydroxide in this solution.

Two or more mole equivalents of base are required to ensure full conversion of the pyridine to pyridone. About 2.2 equivalents have been found generally satisfactory, based on pure pyridine starting material. Thus, the normal working range will be from 2 to 3, preferably from 2.1 to 2.3, equivalents of base to pyridine starting material. However, to enable the process to be operated at higher temperatures at atmospheric pressure, either a greater strength or a greater excess of alkali metal hydroxide, or both, may be used. For example, 2.2 to 2.3 mole equivalents of about 50% w/v strength potassium hydroxide will enable the process to be operated at temperatures up to 130° C., while 14 mole equivalents of about it 80% strength potassium hydroxide allows the process to be operated at temperatures up to about 150° C.

The temperature of the reaction should be in the range of 50° C. to 160° C. and will normally be in the range of 80° C. to 130° C. Temperatures of 90° C. to 130° C. are favoured.

When a temperature above 100° C. is used, the reaction can be carried out either at atmospheric pressure by using a greater strength and/or greater excess of alkali metal hydroxide as previously discussed, or at higher pressures in a sealed vessel, for example, in an autoclave whose material of construction can withstand the effects of aqueous alkali at temperatures of up to 160° C. and the autogenous pressures generated. Suitably such a vessel is constructed from a nickel alloy such as inconel, monel or hastelloy. Normally pressures of 4 to 5 bar are generated at temperature of 150° C. to 160° C.

The process is conveniently carried out by adding the pyridine or mixed pyridine starting material to a stirred aqueous solution of an alkali metal hydroxide and heating the resulting two-phase reaction mixture to a temperature of between 80° C. and 130° C., typically 100° C. to 130° C., at atmospheric pressure. The progress of reaction may be followed by the periodic analysis of samples using, for instance, qualitative gas chromatography. When the reaction is adjudged complete, the reaction mixture is acidified and the pyridone isolated by filtration and washed and dried as required. In a preferred recovery procedure, the reaction mixture is acidified to about pH 5 using, for example, an inorganic acid such as concentrated hydrochloric acid, while maintaining the temperature at about 40° C., for instance from 35° C. to 45° C. It is then cooled to about 10° C., for instance from 5° C. to 15° C., before the product is isolated.

While these procedures are convenient, they are not limiting on the operation of the invention process. Thus the starting material may be added progressively to the aqueous base or vice versa; or the two may be added together in an "all-in" process. The progressive addition of starting material to aqueous base (either continuously or gradually in portions) has been found particularly effective in controlling the reaction exotherm generated in large-scale production. Alternatively, it may be possible to feed streams of the starting material and base together into a reactor in a continuous or semi-continuous process. In addition, it may be advantageous, particularly when a high level of chlorinated pyridine component is present in the starting material, to employ a solvent as previously described (this can assist in solubilising a mixed pyridine starting material), or to increase the temperature by allowing the pressure to rise or to increase the concentration of the alkali metal hydroxide. It may also be advantageous to use a phase transfer catalyst such as a quaternary ammonium or phosphonium salt, for example tetrabutylammonium bromide, or a crown ether or a polyethylene glycol variant, or a catalyst such as potassium iodide.

The process of the invention is particularly suitable for preparing 2-hydroxy-6-trifluoromethylpyridine from 2-fluoro-6-trifluoromethylpyridine, which is either pure or contains 2-chloro-6-trifluoromethylpyridine as a minor component or impurity. Typically a mixed,d 2-fluoro-/2-chloro-starting material will contain the components in the ratio of from 95:5 to 99.9:0.1. The process is, however, equally useful for hydrolysing mixed pyridine starting materials, for example, ones containing up to 50% or more of chlorinated material.

The 2-fluoro-6-trifluoromethylpyridine starting material is a known compound (Chemical Abstracts Registry No. 94238-04-0) disclosed in U.S. Pat. No. 4,474,599. 2-Chloro-6-trifluoromethylpyridine is also a known compound and its preparation is described in EP-A-0042696, EP-A-0110690 and U.S. Pat No. 3,682,936.

The invention is illustrated by the following Examples in which g=grammes ml=millilitre ° C. =degrees centigrade ml=millilitre mp=melting point NMR=nuclear magnetic resonance GC=gas chromatography reacting

EXAMPLE 1

This Example illustrates the preparation of 2-hydroxy-6-trifluoromethylpyridine by reacting 2-fluoro-6-trifluoromethylpyridine with aqueous potassium hydroxide at 100° C. Potassium hydroxide (95%, 20.5 g, 2.22 mole equivalents) and water (180 ml) were charged to a 500 ml round bottomed flask equipped with mechanical stirrer, reflux condenser and contents thermometer. 2-Fluoro-6-trifluoromethylpyridine (26.0 g, 99.5% strength) was charged to the aqueous base. The resulting two-phase solution was heated to 100° C. The reaction mixture was sampled after 2 hours at 100° C. and qualitative GC analysis showed 19.29 area % 2-hydroxy-6-trifluoromethylpyridine and 78.9 area % 2-fluoro-6-trifluoromethylpyridine. The reaction mixture was left to stir for an additional 3 hours at 100° C. before being resampled. Qualitative GC analysis showed 99.51 area % 2-hydroxy-6-trifluoromethylpyridine and 0.12 area % 2-fluoro-6-trifluoromethylpyridine. The reaction mixture was cooled to below 10° C. and acidified to pH 5 (using pH paper) with concentrated hydrochloric acid (36%, 21.7 g, 1.36 mole equivalents) while maintaining the temperature below 10° C. A white product was isolated by filtration and the filtrates used to wash out the flask. The filter cake was sucked dry, washed with cold water (29.1 g) and sucked dry again. The product was dried in an evacuated oven at 40° C. overnight: isolated dry weight 23.93 g at 97.74%; yield, 91.4%; NMR $^1$H and $^{13}$C conforms to structure; mp (Gallenkamp melting point apparatus) 126.7–127.6° C.

EXAMPLE 2

This Example further illustrates the preparation of 2-hydroxy-6-trifluoromethylpyridine by reacting 2-fluoro-6-trifluoromethylpyridine with aqueous potassium hydroxide at 100° C.

Potassium hydroxide (95%, 20.5 g, 2.22 mole equivalents) and water (80 ml) were charged to a 250 ml round bottomed flask equipped with mechanical stirrer, reflux condenser and contents thermometer. 2-Fluoro-6-trifluoromethylpyridine (26.0 g, 99.5% strength) was charged to the aqueous base. The resulting two-phase solution was heated to 100° C. The reaction mixture was sampled after 2 hours at 100° C. and qualitative GC analysis showed 90.96 area % 2-hydroxy-6-trifluoromethylpyridine and 9.03 area % 2-fluoro-6-trifluoromethylpyridine. The reaction mixture was left to stir for an additional 2 hours at 100° C. before being resampled. Qualitative GC analysis showed 98.59 area % 2-hydroxy-6-trifluoromethylpyridine and 1.39 area % 2-fluoro-6-trifluoromethylpyridine. After stirring another hour, the reaction mixture was cooled to below 10° C. and acidified to pH 5 (using pH paper) with concentrated hydrochloric acid (36%, 21.2 g, 1.33 mole equivalents) while maintaining the temperature below 10° C. A white product was isolated by filtration and the filtrates used to wash out the flask. The filter cake was sucked dry, washed with cold water (20 g) and sucked dry again. The product was dried in an evacuated oven at 40°C. overnight: isolated dry weight 25.43 g at 87.79%; yield 87.2%.

EXAMPLE 3

This Example illustrates the preparation of 2-hydroxy-6-trifluoromethylpyridine by reacting 2-fluoro-6-trifluoromethylpyridine with aqueous potassium hydroxide at 80° C. Potassium hydroxide (95%, 2.6 g, 2.20 mole equivalents) and water (22.5 g) were charged to a 100 ml round bottomed flask equipped with mechanical stirrer, reflux condenser and contents thermometer. 2-Fluoro-6-trifluoromethylpyridine (3.3 g, 99.5% strength) was charged to the aqueous base. The resulting two-phase solution was heated to 80° C. The reaction mixture was sampled after 13 hours at 80° C. and qualitative GC analysis showed 47.3 area % 2-hydroboxy-6-trifluoromethylpyridine and 46.2 area % starting material.

EXAMPLE 4

This Example illustrates the preparation of 2-hydroxy-6-trifluoromethylpyridine by reacting 2-fluoro-6-trifluoromethylpyridine with aqueous sodium hydroxide at 100° C. Sodium hydroxide (98%, 1.8 g, 2.20 mole equivalents) and water (16.2 g) were charged to a 100 ml round bottomed flask equipped with mechanical stirrer, reflux condenser and contents thermometer. 2-Fluoro-6-trifluoromethylpyridine (3.3 g 99.5% strength) was charged to the aqueous base. The resulting two-phase solution was heated to 100° C. The reaction mixture was sampled after 12 hours at 100° C. and 48 hours stirring at ambient temperature. Analysis by qualitative GC showed 99.65 area % 2-hydroxy-6-trifluoropyridine and no starting material.

EXAMPLE 5

This Example illustrates the preparation of 2-hydroxy-6-trifluoromethylpyridine by reacting a 50:50 mixture of 2-fluoro-6-trifluoromethylpyridine and 2-chloro-6-trifluoromethylpyridine with aqueous potassium hydroxide at 100–105°C. Potassium hydroxide flake (95%, 13.0 g, 2.22 mole equivalents), and water (113.9 g) were charged to a 250 ml round bottomed flask fitted with a condenser, agitator and contents thermometer. The contents were stirred to give a solution. 2-Fluoro-6-trifluoromethylpyridine (99.7%, 8.27 g, 0.5 mole equivalents) and 2-chloro-6-trifluoromethylpyridine (99.0%, 9.17 g, 0.5 mole equivalents) were added and the reaction mixture heated to 100° C. During the reaction the temperature rose to 105° C. The reaction mixture was sampled and analysed and found to contain 0.9% 2-fluoro-6-trifluoromethylpyridine and 98.4 % 2-hydroxy-6-trifluoromethylpyridine. No 2-chloro-6-trifluoromethylpyridine was present. The reaction mixture was cooled to 5° C. Concentrated hydrochloric acid (36.0%, 14.2 g) was added dropwise over 40 minutes and the temperature maintained below 5° C. The product slurry was stirred for a further 60 minutes at less than 5° C. The product was filtered and displacement washed with water (18.5 g). The title product was then dried under vacuum at 40° C.: isolated dry weight 12.9 g, strength 99.0%; isolated yield 78.3%.

EXAMPLE 6

This Example illustrates the preparation of 2-hydroxy-6-trifluoromethylpyridine by reading a 50:50 mixture of 2-fluoro-6-trifluoromethylpyridine and 2-chloro-6-trifluoromethylpyridine with aqueous potassium hydroxide at 150° C. Potassium hydroxide flake (95%, 82.1 g, 13.9 mole equivalents) and water (19.5 g) were charged to a 250 ml round bottom flask fitted with a condenser, agitator and contents thermometer. The contents were stirred to give a solution. 2-Fluoro-6-trifluoromethyl-pyridine (99.7%, 8.27 g, 0.5 mole equivalents) and 2-chloro-6-trifluoromethylpyridine (99.0%, 9.17 g, 0.5 mole equivalents) were added and the reaction mixture heated to 150° C. and held for 2 hours. The reaction mixture was sampled and analysed and found to contain 0.6%, 2-fluoro-6-trifluoromethylpyridine and 99.4% 2-hydroxy-6-trifluoromethylpyridine. No 2-chloro-6-trifluoromethylpyridine was present. The reaction mixture was cooled to 5° C. and water (40 g) added. Concentrated hydrochloric acid (36%, 80.0 g) was added dropwise over 40 minutes and the temperature maintained below 5° C. The product slurry was stirred for a further 60 minutes at less than 5° C. The product was filtered and displacement washed with water (18.5 g x2). The title product was then dried under vacuum at 40° C.: isolated dry weight 14.8 g (assumed strength 100%); isolated yield 90.8%.

EXAMPLE 7

This Example illustrates the preparation of 2-hydroxy-6-trifluoromethylpyridine by reacting a 50:50 mixture of 2-fluoro-6-trifluoromethylpyridine and 2-chloro-6-trifluoromethylpyridine with solid potassium hydroxide and t-amyl alcohol at 105–108° C. Potassium hydroxide flake (95%, 13.0 g, 2.22 mole equivalents) and t-amyl alcohol (99%, 73.9 g, 8.32 mole equivalents) were charged to a 250 ml round bottomed flask fitted with a condenser, agitator and contents thermometer. The contents were stirred to give a slurry. 2-Fluoro-6-trifluoromethylpyridine (99.7%, 8.27 g, 0.5 mole equivalents) and 2-chloro-6-trifluoromethylpyridine (99.0%, 9.17 g, 0.5 mole equivalents) were added and the reaction mixture heated to 105° C. (slight reflux). During the reaction the temperature rose to 108° C. The reaction mixture was sampled after 4 hours and found to contain 0.2% 2-fluoro-6-trifluoromethylpyridine and 93.6% 2-hydroxy-6-trifluoromethylpyridine. No 2-chloro-6-trifluoromethylpyridine was present. The reaction mixture was cooled to 80° C. t-Amyl alcohol was distilled off to 108° C. and the reaction mixture was cooled to 40° C. Water (4.6 g) was added. Water and t-amyl alcohol were distilled off to a temperature of 110° C. The reaction mixture was cooled to 50° C. and water (79.6 g) was added. The reaction was cooled to 5° C. and concentrated hydrochloric acid (36.0%, 14.2 g) added dropwise over 40 minutes while the temperature was maintained below 5° C. The product slurry was stirred for a further 60 minutes at less than 5° C. The product was filtered off and displacement washed with water (18.5 g). The title product was then dried under vacuum at 40° C.: isolated dry ,weight 8.2 g, strength 97.5%; isolated yield 49.0% (residual t-amyl alcohol left after distillation led to yield losses).

EXAMPLE 8

This Example illustrates the preparation of 2-hydroxy-6-trifluoromethylpyridine by reacting a 95:5 mixture of 2-fluoro-6-trifluoromethylpyridine and 2-chloro-6-trifluoromethylpyridine with aqueous potassium hydroxide at 115–130° C. Potassium hydroxide flake (95%, 25.9 g, 2.22 mole equivalents) and water (24.6 g, 6.84 mole equivalents) were charged to a 250 ml round bottomed flask fitted with a condenser, agitator and (contents thermometer. The contents were stirred to give a solution and heated to 130° C. (reflux). A mixture of 2-fluoro-6-trifluoromethylpyridine (99.2%, 31.6 g, 0.95 mole equivalents) and 2-chloro-6-trifluoromethylpyridine (100%, 1.8 g, 0.05 mole equivalents) was add d dropwise over 1 hour maintaining a gentle reflux (115–120° C.). When the addition was complete the reaction mixture was held for 4 hours at 115° C. (reflux). The reaction mixture was cooled to 50° C. and water (79 g) added. Hydrochloric acid (approximately 27.4 g, 36% strength) was then added dropwise over 30 minutes maintaining a temperature of 50° C. to give a pH of 5. The resulting slurry was stirred for a further 10 minutes at 50° C. and then cooled to 0–5° C. and the pH readjusted to 5. The slurry was held for a further 30 minutes at 0–5° C. The product was filtered and displacement washed with water (37 g). The title product was then dried under vacuum at 40° C.: isolated dry weight 31.7 g, yield 97% (assuming a product strength of 100%).

EXAMPLE 9

This Example illustrates the preparation of 2-hydroxy-6-trifluoromethylpyridine by reacting 2-fluoro-6-trifluoromethylpyridine with aqueous potassium hydroxide (35%) at 100° C.

Potassium hydroxide (95%, 33.8 g, 2.2 mole equivalents) and water (63.2 g) were charged to a 250 ml round bottomed flask equipped with mechanical stirrer, reflux condenser and contents thermometer. The contents were stirred to give a solution, and heated to 100° C. 2-Fluoro-6-trifluoromethylpyridine (42.5 g. 99.2% strength) was added dropwise over 133 minutes maintaining the reaction temperature at 100° C. The reaction mixture was sampled at the end of the addition, and qualitative GC analysis showed 92.8 area % 2-hydroxy-6-trifluoromethylpyridine and 6.5 area % starting material.

EXAMPLE 10

This Example illustrates the preparation of 2-hydroxy-6-trifluoromethylpyridine by reacting 2-fluoro-6-trifluoromethylpyridine with aqueous potassium hydroxide (35%) at 100° C., using 'staggered' aliquot additions of 2-fluoro-6-trifluoromethylpyridine in order to control the exotherm resulting from the reaction.

Potassium hydroxide (95%, 34 g, 2.25 mole equivalents) and water (63.2 g) were charged to a 250 ml round bottomed flask equipped with mechanical stirrer, reflux condenser and contents thermometer. The contents were stirred to give a solution, and heated to 100° C. 2-Fluoro-6-trifluoromethylpyridine (42 g, 99.2% strength) was charged to the aqueous base in five equal aliquots (8.5 g) over a period of 115 minutes, maintaining the reaction temperature at 100° C. The exact timing of the additions is detailed in the table below.

| Aliquot# | Time (minutes) |
|---|---|
| 1 | 0 |
| 2 | 40 |
| 3 | 68 |
| 4 | 91 |
| 5 | 115 |

Following each aliquot addition, a distinct exotherm was observed, and the reaction mixture was allowed to cool back to 100° C. before continuing with the next aliquot addition. The reaction mixture was sampled 8 minutes after the end of the addition, and qualitative GC analysis showed 79.8 area % 2-hydroxy-6-trifluoromethylpyridine and 20.2 area % starting material. After a further 59 minutes at 100° C., the reaction mixture was again sampled, and qualitative GC analysis showed 100 area % 2-hydroxy-6-trifluoromethylpyridine.

What is claimed is:

1. A process for the preparation of 2-hydroxy-6-trifluoromethylpyridine which comprises reacting 2-fluoro-6-trifluoromethylpyridine or a mixture of 2-fluoro-6-trifluoromethylpyridine and 2-chloro-6-trifluoromethylpyridine with an alkali metal hydroxide at a temperature of from 50° C. to 160° C. in the absence of an organic solvent and acidifying the product so formed.

2. A process according to claim 1 wherein the alkali metal hydroxide is in the form of an aqueous solution.

3. A process according to claim 2 wherein the strength of the aqueous alkali metal hydroxide is in the range of 9% to 85% w/v.

4. A process according to claim 1 wherein the alkali metal hydroxide is potassium hydroxide.

5. A process according to claim 1 wherein the amount of alkali metal hydroxide used is in the range of from 2 to 3 equivalents of base to the sum of the 2-fluoro-6-trifluoromethylpyridine and 2-chloro-6-trifluoromethylpyridine starting material.

6. A process according to claim 1 wherein the 2-hydroxy-6-trifluoromethylpyridine or mixture of 2-fluoro-6-trifluoromethylpyridine and 2-chloro-6-trifluoromethylpyridine is added progressively to the aqueous alkali metal hydroxide.

7. A process for the preparation of 2-hydroxy-6-trifluoromethylpyridine which comprises reacting 2-fluoro-6-trifluoromethylpyridine with an aqueous alkali metal hydroxide at a temperature of from 80° C. to 150° C. and acidifying the product so formed.

8. A process according to claim 7 wherein the temperature is in the range of from 90° C. to 130° C.

9. A process for the preparation of 2-hydroxy-6-trifluoromethylpyridine which comprises reacting 2-fluoro-6-trifluoromethylpyridine or a mixture of 2-fluoro-6-trifluoromethylpyridine and 2-chloro-6-trifluoromethylpyridine with an alkali metal hydroxide at a temperature of from 50° C. to 160° C., in the absence of an organic solvent acidifying the product so formed at a temperature of from 35° C. to 45° C. and isolating the resultant 2-hydroxy-6-trifluoromethylpyridine at a temperature of from 5° C. to 15° C.

* * * * *